United States Patent
Tu et al.

[11] Patent Number: 5,980,563
[45] Date of Patent: Nov. 9, 1999

[54] ABLATION APPARATUS AND METHODS FOR TREATING ATHEROSCLEROSIS

[76] Inventors: Lily Chen Tu; Hosheng Tu, both of 2151 Palermo, Tustin, Calif. 92782

[21] Appl. No.: 09/143,890

[22] Filed: Aug. 31, 1998

[51] Int. Cl.[6] .................................................. A61B 17/39
[52] U.S. Cl. .............................. 607/113; 607/101; 606/41
[58] Field of Search ................................ 607/96, 98, 99, 607/101–102, 113; 606/41, 42

[56] References Cited

U.S. PATENT DOCUMENTS

| | | | |
|---|---|---|---|
| 5,456,662 | 10/1995 | Edwards et al. | |
| 5,507,743 | 4/1996 | Edwards et al. | 606/41 |
| 5,546,954 | 8/1996 | Yamada | |
| 5,853,409 | 12/1998 | Swanson et al. | 606/31 |
| 5,876,398 | 3/1999 | Mulier et al. | 606/41 |
| 5,921,982 | 7/1999 | Lesh et al. | 606/41 |

OTHER PUBLICATIONS

G. Spera "The Next Wave in Minimally Invasive Surgery" Medical Device & Diagnostic Industry pp. 36–44 Aug. 1998.

*Primary Examiner*—Linda C. M. Dvorak
*Assistant Examiner*—Roy Gibson

[57] ABSTRACT

An ablation apparatus for treating tissues or atherosclerosis on a patient having a pre-implanted medical stent, the ablation apparatus including an elongate tubular shaft having a deployable spiral wire electrode at its distal end adapted to contact the stent and to apply RF energy to the tissue underlying the stent for therapeutic purposes.

20 Claims, 5 Drawing Sheets

ABLATION APPARATUS AND METHODS FOR TREATING ATHEROSCLEROSIS

The present invention generally relates to improved medical apparatus and methods for treating vascular tissues, and more particularly, to such an ablation apparatus and methods for treating atherosclerosis or tissues in a patient by delivering therapeutic RF energy through a metal stenting element to the specific lesion sites.

BACKGROUND OF THE INVENTION

An artery is one of the tube-shaped blood vessels that carries blood away from the heart to the body's tissues and organs. An artery is made up of outer fibrous layer, smooth muscle layer, connecting tissue and the inner lining cells. If arterial walls become hardened due to the accumulation of fatty substances, then blood flow can be diminished. Hardening of the arteries, or loss of vessel elasticity, is termed arteriosclerosis while fatty deposit build-up is termed atherosclerosis. Atherosclerosis and its complications are a major cause of death in the United States. Heart and brain diseases are often the direct result of this accumulation of fatty substances that impair the arteries' ability to nourish vital body organs.

Balloon angioplasty is a nonsurgical method of clearing coronary and other arteries, blocked by atherosclerotic plaque, fibrous and fatty deposits on the walls of arteries. A catheter with a balloon-like tip is threaded up from the arm or groin through the artery until it reaches the blocked area. The balloon is then inflated, flattening the plaque and increasing the diameter of the blood vessel opening. The arterial passage is thus widened. As a result of enlarging the hardened plaque, cracks may unfortunately occur within the plaque to expose the underlying fresh tissue or cells to the blood stream There are limitations, however, to this technique's application, depending on the extent of the disease, the blood flow through the artery, and the part of the anatomy and the particular vessels involved. Plaque build-up and/or severe re-stenosis recurs within 6 months is up to 30–40 percent of those treated. Balloon angioplasty can only be characterized as a moderate-success procedure. Recently, a newer technique of inserting a metallic stenting element is used to permanently maintain the walls of the vessel treated at its extended opening state. Vascular stents are tiny mesh tubes made of stainless steel or other metals and are used by heart surgeons to prop open the weak inner walls of diseased arteries. They are often used in conjunction with balloon angioplasty to prevent restenosis after the clogged arteries are treated. Stenting technique reduces the probability of restenosis, however, the success rate is still sub-optimal. The underlying fresh tissue or cells still pose as a precursor for vessel reclosures or angio-spasm.

When a clogged artery is widened, the plaque is broken up and the underlying collagen or damaged endothelium is exposed to the blood flow. Collagen has a prothrombotic property which is part of body healing process. Unless the collagen or the damaged endothelium is passivated or modulated, the chance for blood vessel clotting as well as restenosis exist. Moderate heat is known to tighten and shrink the collagen tissue as illustrated in U.S. Pat. No. 5,456,662 and U.S. Pat. No. 5,546,954. It is also clinically verified that thermal energy is capable of denaturing the tissue and modulating the collagenous molecules in such a way that treated tissue becomes more resilient ("The Next Wave in Minimally Invasive Surgery" MD&DI pp. 36–44, August 1998). Therefore, it becomes imperative to post-treat vessels walls after the walls are treated with angioplasty and/or stenting procedures.

One method of reducing the size of cellular tissues in situ has been used in the treatment of many diseases, or as an adjunct to surgical removal procedures. This method applies appropriate heat to the tissues, and causes them to shrink and tighten. It can be performed on a minimal invasive fashion, which is often less traumatic than surgical procedures and may be the only alternative method, wherein other procedures are unsafe or ineffective. Ablative treatment apparatus have an advantage because of the use of a therapeutic energy that is rapidly dissipated and reduced to a non-destructive level by conduction and convection, to other natural processes.

RF therapeutic protocol has been proven to be highly effective when used by electrophysiologists for the treatment of tachycardia; by neurosurgeons for the treatment of Parkinson's disease; and by neurosurgeons and anesthetists for other RF procedures such as Gasserian ganglionectomy for trigeminal neuralgia and percutaneous cervical cordotomy for intractable pains. Radiofrequency treatment, which exposes a patient to minimal side effects and risks, is generally performed after first locating the tissue sites for treatment. Radiofrequency energy, when coupled with a temperature control mechanism, can be supplied precisely to the apparatus-to-tissues contact site to obtain the desired temperature for treating a tissue.

A stent deployed within a vessel, such as a coronary stent, has excellent metal-totissue contact surface. It becomes an ideal medium for applying thermal energy to the tissue needed for treatment or modulation. In the case of angioplasty alone, the enlarged blood vessel still needs certain metallic contact surface for delivering the RF thermal energy to the denuded collagen or damaged endothelium. A temporary metallic stenting element is useful in this case to shrink and tighten the target tissue. Therefore, there is a need for an improved medical apparatus having the capability to effectively contact the inner walls of a tubular vessel using the radiofrequency energy to treat an enlarged artery or other tissues, such as esophagus, larynx, ureter, urethra and the like.

SUMMARY OF THE INVENTION

In general, it is an object of the present invention to provide a method and an improved medical ablation apparatus for generating heat, to treat the atherosclerosis, vascular vessels, or other tissues, such as intestine, colon, ureter, uterine tube, and the like. It is another object of the present invention to provide a method and an apparatus for monitoring the temperature of the ablated tissue, and to control the temperature by utilizing a temperature control mechanism and/or algorithm. The location of the temperature sensor means is preferably at close proximity of the electrode means of the ablation apparatus. It is still another object of this invention to provide a method and an apparatus for treating atherosclerosis, vascular walls, or tubular cellular tissues in a patient by applying RF current to a pre-implanted stent and consequently to the underlying tissues.

Briefly, heat is generated by supplying a suitable energy source to an apparatus, which is comprised of at least one electrode means, in contact with the body tissues through a pre-implanted stent. A "pre-implanted stent" is defined in this invention as any metallic stenting element, in mesh form, coil form or other appropriate form, used to enlarge and maintain the enlarged tissues or vessels. Examples include coronary stent, peripheral stent, uterine stent and the like. A suitable energy source may consist of radiofrequency energy, microwave energy, ultrasonic energy, alternating current energy, or laser energy. The energy can be applied to the stent and consequently to the atherosclerosis, vascular walls, or cellular tissues through the electrode means. A DIP (dispersive indifferent pad) type pad or electrode, that contacts the patient, is connected to the Indifferent Electrode Connector on the RF generator. Therefore, the RF energy delivery becomes effective when a close circuit from a RF generator through a patient and returning to the RE generator is formed. When using an alternating current outlet, the generator should be grounded to avoid electrical interference. Heat is controlled by the power of the RF energy delivered and by the delivery duration. The standard RE energy generator means and its applications through the electrode means, to a patient are well known for those who are skilled in the art.

In an optional embodiment, means for generating vibration at the distal section comprises a motor mounted in the cavity of the handle, which has a rotatable motor shaft, an elongated connecting shaft having a first end, to which the distal end portion is connected, and a second end connected to the handle, a weight eccentrically mounted on the motor shaft with respect to the motor shaft axis, so as to rotate eccentrically, so that when the motor shaft rotates, the distal end portion of the apparatus vibrates.

In one embodiment, the apparatus comprises a deployable wire electrode or plurality of wire electrodes. In a preferred embodiment, the wire electrode is a spiral wire electrode having the next spiral always larger than the prior spiral, so that resilience and semi-compressibility becomes the property of the wire electrode to ultimately deploy to its full extent. The deployed wire electrode is to intimately contact a pre-implanted stent at any contact point and subsequently the stent becomes an electrode means because the stent contacts the tissues behind itself. The wire electrode is connected to an external RF generating means through an electrical conductor. In the case of a wire electrode inside a tubular vessel, the wire electrode is preshaped and extends to its maximum distance radially to contact the pre-implanted stent The wire electrode is semi-compressible so that when the deployed wire is pressed against the stent, an appropriate pressure is exerted onto the stent to ensure intimate contact when applying the RF energy therapy.

The method and medical apparatus of the present invention has several significant advantages over other known systems or techniques to treat the atherosclerosis or tissues having at least one pre-implanted stent. In particular, the apparatus system comprising the extendible wire electrode means, using RF energy as a heat source, in this invention and simultaneously applying pressure to the pre-implant stent, results in a more efficient therapeutic effect, which is highly desirable in its intended application on the atherosclerosis or on other tissue ablation applications when there is a pre-implanted stent.

BRIEF DESCRIPTION OF THE DRAWINGS

Additional objects and features of the present invention will become more apparent and the invention itself will be best understood from the following Detailed Description of Exemplary Embodiments, when read with reference to the accompanying drawings.

DETAILED DESCRIPTION OF EXEMPLARY EMBODIMENTS

Referring to FIGS. 1 to 5, what is shown is an embodiment of the ablation apparatus system, comprising simultaneously applying radiofrequency energy and applying a pressure therapy to treat the atherosclerosis, vascular vessels, or other tubular cellular tissues of a patient through a pre-implanted stent.

Figure 1:
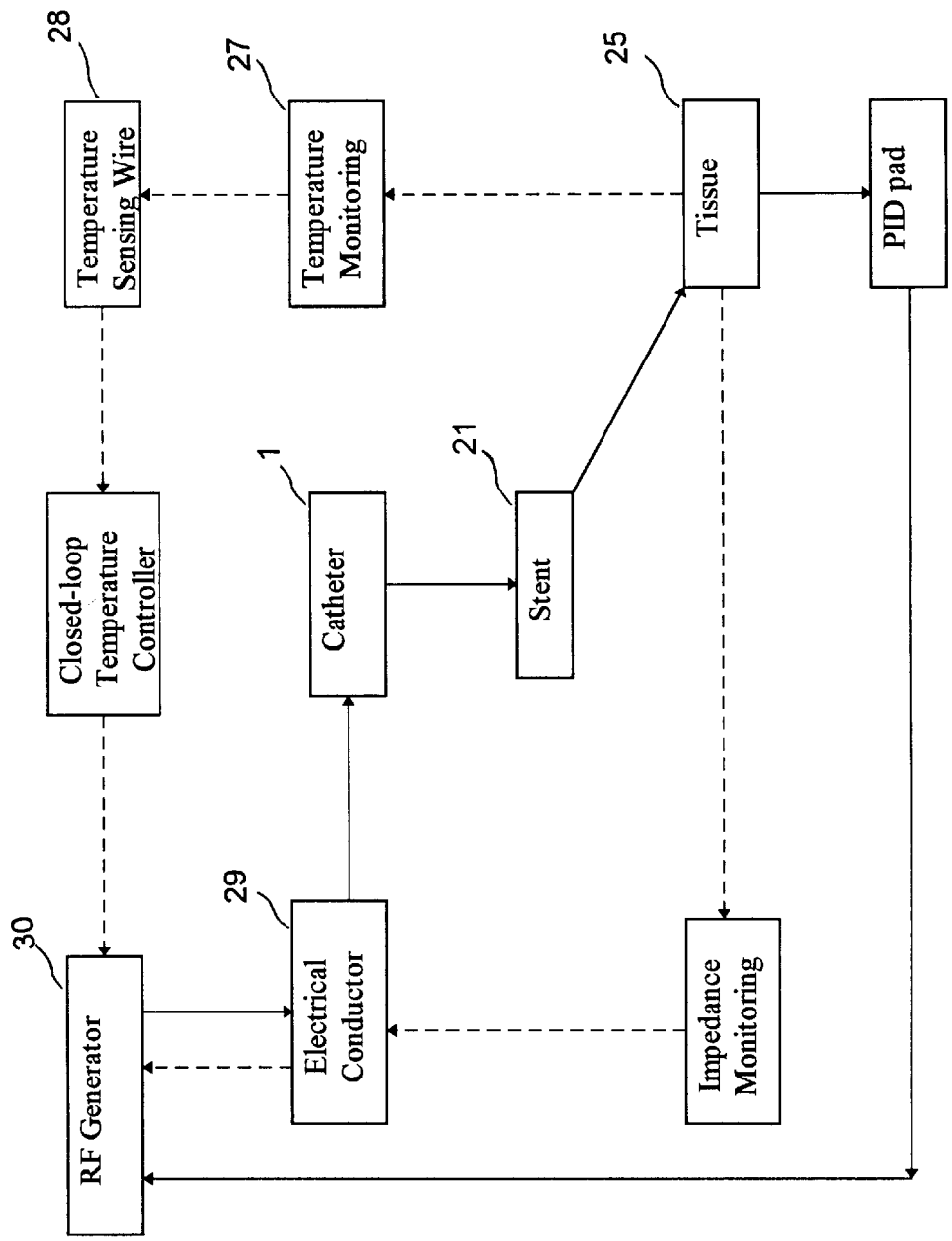
FIG. 1 is a schematic diagram of a RF treatment method in relation to the tissues or atherosclerosis through a pre-implanted metallic stent in a patient.

FIG. 1 shows a schematic diagram of a RF treatment method in relation to the tissues or atherosclerosis through a pre-implanted metallic stent in a patient. a RF generator 30 is connected to a catheter or an ablation apparatus 1 through an electrical conductor 29. A wire electrode 12 of the catheter or an ablation apparatus 1 is to contact a pre-implanted stent 21 when the apparatus is deployed. The stent is in close contact with the underlying tissue 25. A DIP (dispersive indifferent pad) type pad, that contacts the patient, is connected to the Indifferent Electrode Connector on the RF generator 30. Therefore, the RF energy delivery becomes effective when a close circuit from a RF generator through a patient and returning to the RF generator is formed. Impedance measured from the tissue contact is to ensure good tissue contact for ablation, otherwise the RF power is cutoff when the impedance is unreasonably high. A temperature sensor 27 is also used to measure the tissue temperature and is relayed through a temperature sensing wire 28 and a closed-loop temperature controller for controlling the ablative energy delivered. Heat is controlled by the power of the RF energy delivered and by the delivery duration.

Figure 2:
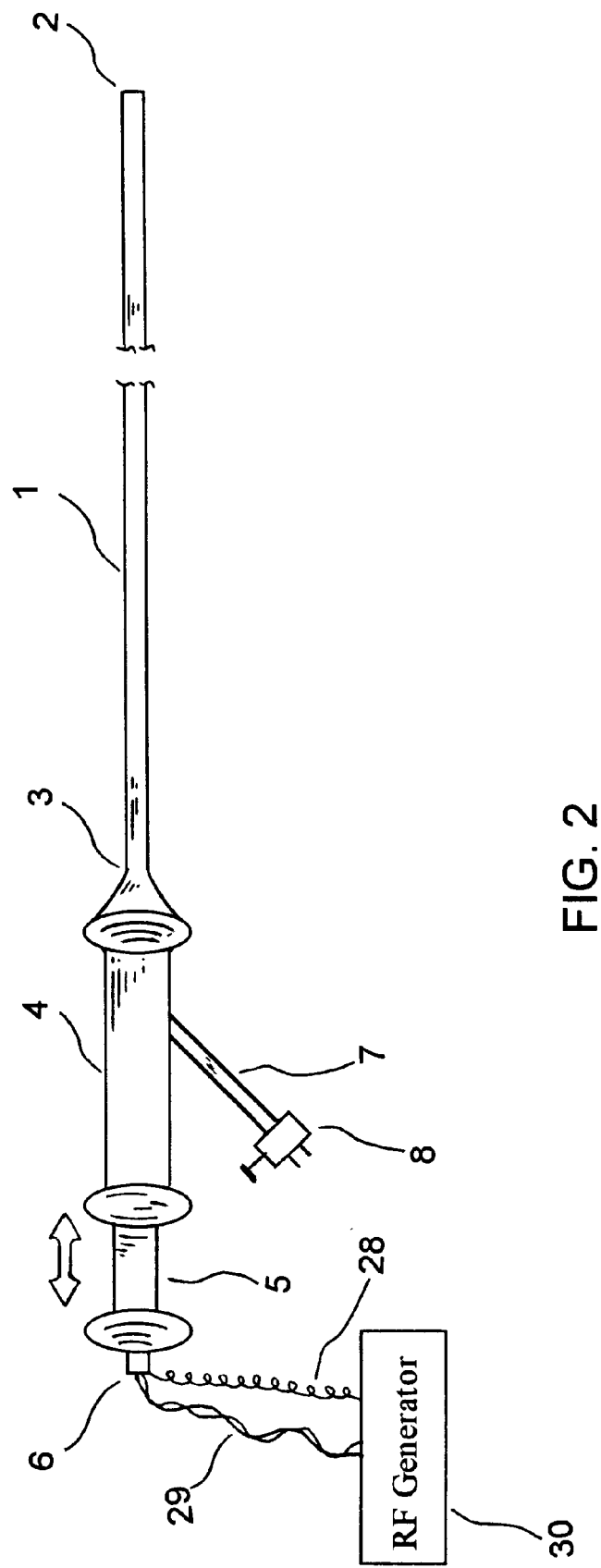
FIG. 2 is an overall view of the ablation apparatus having a deployable wire electrode and RF generator, constructed in accordance to the principles of the present invention.

As shown in FIG. 2, the ablation apparatus system in the form of an elongate tubular assembly 1 comprises a tubular shaft having a distal section, a distal end 2, a proximal end 3, and at least one lumen 10 or 11 extending therebetween, wherein the at least one lumen has at least one opening at the distal end of the tubular shaft 1. A handle 4 is attached to the proximal end 3 of the tubular shaft, wherein the handle 4 has a cavity. A hollow tubing 7 having a passageway and a locking valve 8 is attached to the handle 4, wherein the passageway is connected to the at least one lumen 11 of the tubular shaft 1. An elongate tubular element is located inside the at least one lumen 10 of the tubular shaft 1, wherein the elongate tubular element comprises a distal end 13 and a proximal end, and wherein the distal end 13 comprises a preshaped spiral wire electrode 12.

In one embodiment, the spiral wire electrode has a plurality of spirals, whereby the diameter of the next spiral is larger than that of the prior spiral. An electrode deployment mechanism 5 is mounted on the handle 4, wherein the electrode deployment mechanism is attached to the proximal end of the elongate tubular element. A RF energy generating means 30 is part of the ablation apparatus system, wherein the RF energy is provided to the spiral wire electrode 12 for therapeutic purposes through the conducting wire 29 and the connector 6 at the proximal end of the handle 4.

Figure 3:
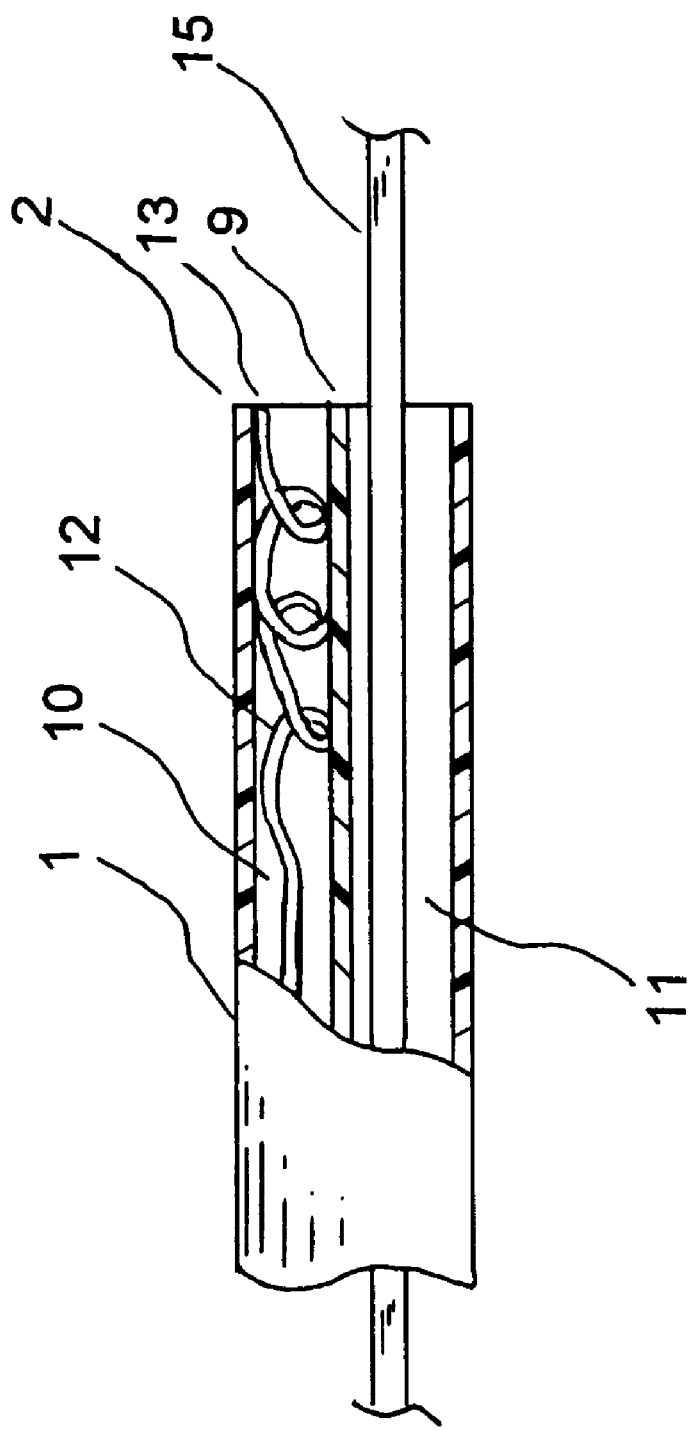
FIG. 3 is a cross-sectional view of the distal end portion of the apparatus, having a deployable wire electrode positioned within the lumen of the tubular shaft, at the non-deployed state.

FIG. 3 shows a cross-sectional view of the distal end portion of the apparatus 1, including a deployable wire electrode 12. Under a non-deployed state, the deployable wire electrode 12 are retracted inside the lumen 10 of the distal end portion. The wire end 13 is located just within the distal end 2 of the tubular shaft 1. In one embodiment, the distal end has two lumens 10 and 11. One lumen 10 is used by the deployable wire electrode 12 for creating an ablation means in association with the pre-implanted stent 21. The other lumen 11 is used to tract a previously inserted guidewire 15 to the lesion site. The apparatus 1 of the present invention rides on the existing guidewire 15 to the target site 24 for ablation operation.

An insulated electrical conductor 29 or the elongate tubular element itself as a conducting means passes through the lumen 10 of the shaft 1 and is connected to the wire electrode means 12. The other end of the electrical conductor means is connected to an external RF generator 30.

Figure 4:
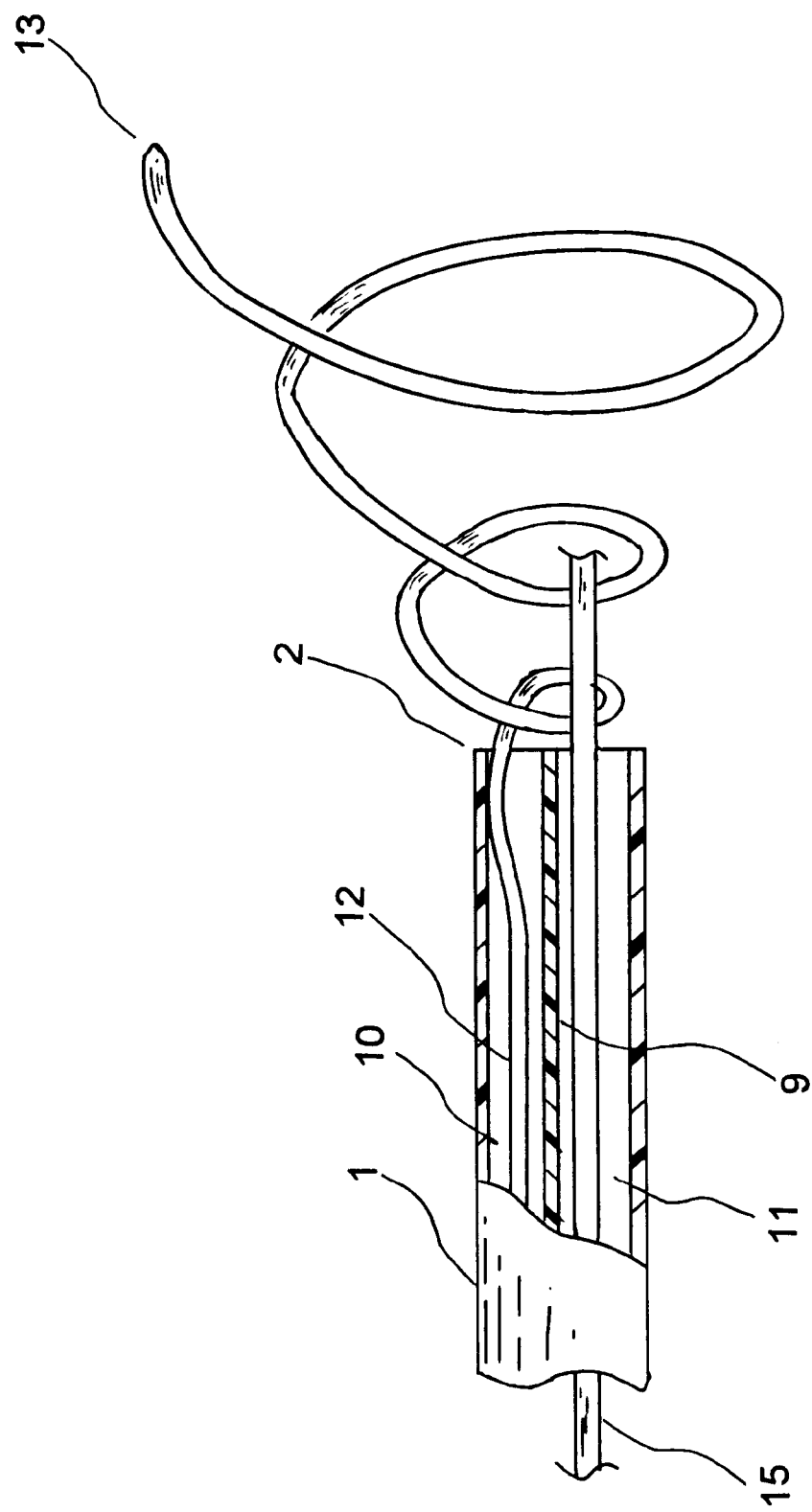
FIG. 4 is a cross-sectional view of the distal end portion of the apparatus, having a deployable wire electrode being deployed to its full extent, at a deployed state.

FIG. 4 shows a cross-sectional view of the distal end portion of the tubular shaft 1 at a deployed state. The deployment operation is initiated at the electrode deployment mechanism 5 at the handle 4. The deployed wire electrode 12 is fully extended radially to contact the inside surface of a pre-implanted stent 21. This distal portion of the deployed wire electrode and its surface is made of conductive material, which is connected to the RF energy source through an insulated electrical conductor. Other portion of the tubular shaft and surface of the apparatus is not conductive. The radially fully extendible spiral wire electrode 12 is extended radially at least twice the diameter of the tubular shaft 1.

In one embodiment, at least one temperature sensing means 27 is disposed at close proximity of the wire electrode 12. Insulated temperature sensor wire means 28 passes from the temperature sensing means 27, to an external temperature control mechanism through the outlet connector 6. The RF energy delivery is controlled by using the measured temperature from the temperature sensing means 27, through a closed-loop temperature control mechanism and/or algorithm. When the measured temperature rises to the preset high-limit point, the temperature control mechanism sends out a signal to cut off the RF energy supply. In a similar maimer, when the measured temperature drops to the preset low-limit point, the temperature control mechanism sends out a signal to activate the RF energy supply.

Figure 5:
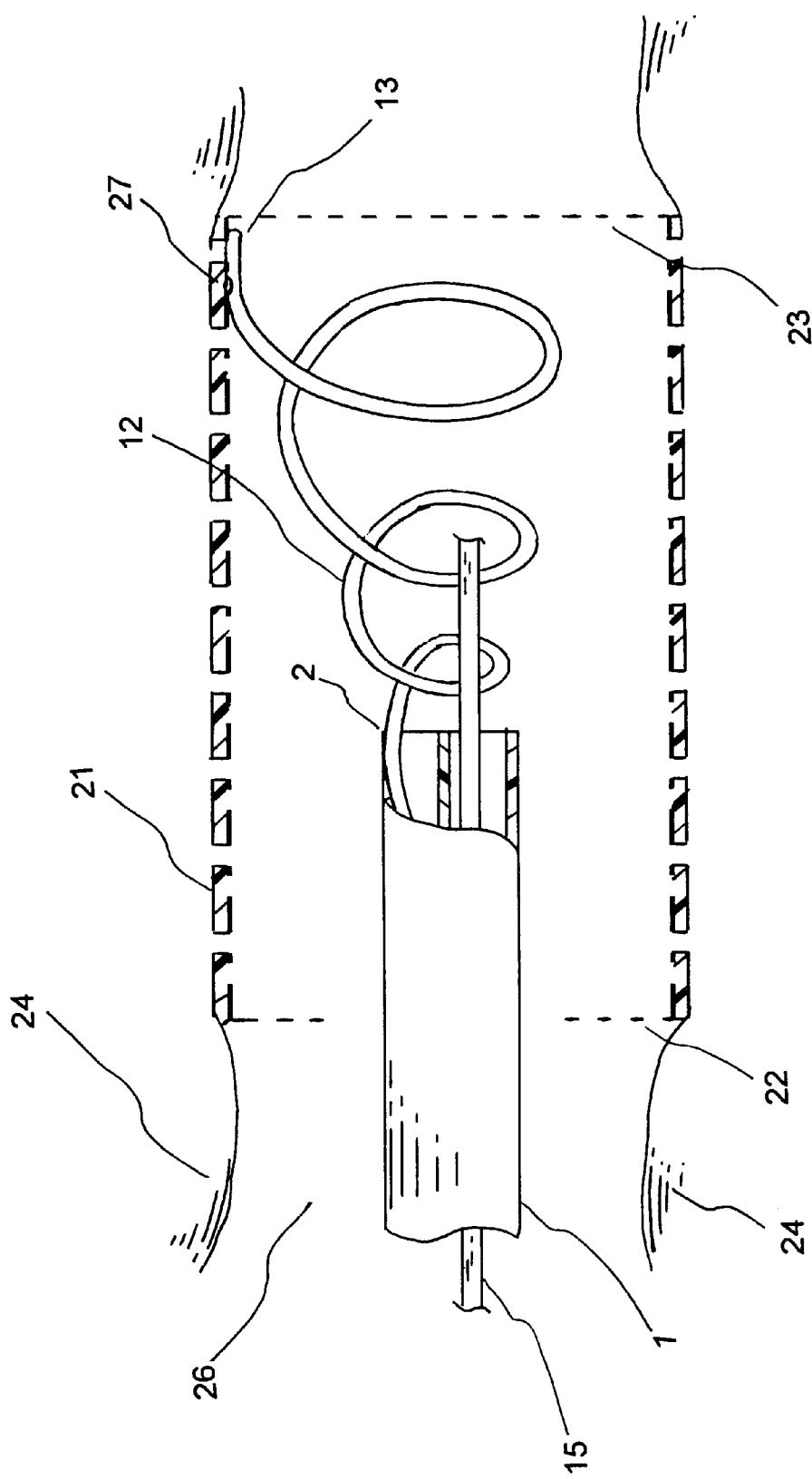
FIG. 5 a perspective view of the tissue underlined behind a pre-implanted stent being treated by the ablation apparatus of the present invention.

FIG. 5 shows a perspective view of a tissue 24 or atherosclerosis behind a pre-implanted stent 21 being treated by the medical ablation apparatus of the present invention. For illustrative purposes, the stenotic artery 26 having an arterial wall 24 is enlarged by an implanted stent 21 in a separate prior procedure. In one embodiment, the stent is bordered by two imaginary lines 22 and 23. To further passivate or modulate the collagen and/or the denuded endothelium cells, RF current is delivered to the wire electrode 12, whereby a portion of the wire electrode 12 contacts the stent 21 at a contact point 27 and forms a "stent-assisted" electrode to treat the atherosclerosis behind the stented region.

During procedures, the ablation apparatus is inserted into the body of a patient through natural opening or a surgical hole. A method for treating tissues of a patient having a pre-implanted medical stent, the method comprising the steps of: (a) inserting an ablation apparatus through a natural opening to the location of the pre-implanted medical stent, wherein the ablation apparatus comprises a tubular shaft having a distal section, a distal end, a proximal end, and at least one lumen extending therebetween, wherein the at least one lumen has at least one opening at the distal end of the tubular shaft; a handle attached to the proximal end of the tubular shaft, wherein the handle has a cavity; a hollow tubing having a passageway and a locking valve attached to the handle, wherein the passageway is connected to the at least one lumen of the tubular shaft; an elongate tubular element located inside the at least one lumen of the tubular shaft, wherein the elongate tubular element comprises a distal end and a proximal end, and wherein the distal end comprises a preshaped wire electrode having a plurality of spirals, wherein the diameter of the next spiral is larger than that of the prior spiral; an electrode deployment mechanism mounted on the handle, wherein the electrode deployment mechanism is attached to the proximal end of the elongate tubular element; (b) deploying the elongate tubular element to radially fully extend the spiral wire electrode, adapted to contact the pre-implanted medical stent; and (c) applying RF energy to the spiral wire electrode to effect treatment of the tissue.

As an alternative illustration, a method for treating atherosclerosis of a patient having a pre-implanted vascular stent, the method comprising the steps of: (a) inserting an ablation apparatus through an artery or a vein to the location of the pre-implanted vascular stent, wherein the ablation apparatus comprises a tubular shaft having a distal section, a distal end, a proximal end, and at least one lumen extending therebetween, wherein the at least one lumen has at least one opening at the distal end of the tubular shaft; a handle attached to the proximal end of the tubular shaft, wherein the handle has a cavity; a hollow tubing having a passageway and a locking valve attached to the handle, wherein the passageway is connected to the at least one lumen of the tubular shaft; an elongate tubular element located inside the at least one lumen of the tubular shaft, wherein the elongate tubular element comprises a distal end and a proximal end, and wherein the distal end comprises a preshaped wire electrode having a plurality of spirals, wherein the diameter of the next spiral is larger than that of the prior spiral; an electrode deployment mechanism mounted on the handle, wherein the electrode deployment mechanism is attached to the proximal end of the elongate tubular element; (b) deploying the elongate tubular element to radially fully extend the spiral wire electrode, adapted to contact the pre-implanted stent; and (c) applying RF energy to the spiral wire electrode to effect treatment of the atherosclerosis.

The external RF energy generator means has the capability to supply RF energy by controlling the time, power, and temperature through an optional separate closed-loop temperature control means. The patient is connected to the RF generator means through a DIP electrode to form a closed-loop current system. Therefore, RF energy is applied and delivered to the targeted atherosclerosis region, through the electrode means of this invention, the "stent-assisted" electrode means. The radiofrequency energy current in this invention is preferably within the range of 50 to 2,000 kHz. The frequency of the vibration of the medical apparatus in this invention is preferably within the range of 60 to 1000 cycles per minute. By simultaneously applying RF energy to the electrode and by applying the pressure therapy, the atherosclerosis can be treated.

In a particular embodiment, the material for the electrode means of this invention consists of conductive metals such as platinum, iridium, gold, silver, stainless steel, Nitinol, or an alloy of these metals.

From the foregoing description, it should now be appreciated that an ablation apparatus system for the tubular organs, atherosclerosis, and the treatment of vascular tissues, comprising a suitable energy source and a pressure therapy has been disclosed. While the invention has been described with reference to a specific embodiment, the description is illustrative of the invention and is not to be construed as limiting the invention. Various modifications and applications may occur to those who are skilled in the art, without departing from the true spirit and scope of the invention, as described by the appended claims.

What is claimed is:

1. An ablation apparatus system comprising:
 a tubular shaft having a distal section, a distal end, a proximal end, and at least one lumen extending therebetween, wherein the at least one lumen has at least one opening at the distal end of the tubular shaft;
 a handle attached to the proximal end of the tubular shaft, wherein the handle has a cavity;
 a hollow tubing having a passageway and a locking valve attached to the handle, wherein the passageway is connected to the at least one lumen of the tubular shaft;
 an elongate tubular element located inside the at least one lumen of the tubular shaft, wherein the elongate tubular element comprises a distal end and a proximal end, and wherein the distal end comprises a preshaped wire electrode having a plurality of spirals, wherein the diameter of the next spiral is larger than that of the prior spiral;
 an electrode deployment mechanism mounted on the handle, wherein the electrode deployment mechanism is attached to the proximal end of the elongate tubular element; and
 a RF energy generating means, wherein the RF energy is provided to the spiral wire electrode for therapeutic purposes.

2. The ablation apparatus system of claim 1, wherein the tubular shaft is made of semi-flexible material.

3. The ablation apparatus system as in claim 1 further comprising at least one temperature sensor, wherein the temperature sensor is disposed at close proximity of the spiral wire electrode of the elongate tubular element.

4. The ablation apparatus system as in claim 1 further comprising a temperature control means, wherein the temperature measured from the temperature sensor is relayed to the temperature control means and is adapted to effect the RF energy supply to the ablation apparatus system.

5. The ablation apparatus system of claim 1, wherein the RF current is within the range of 50 to 2,000 kHz.

6. The ablation apparatus system of claim 1, wherein the material for the spiral wire electrode is selected from the group consisting of platinum, iridium, gold, silver, stainless steel, Nitinol, or an alloy of their mixtures.

7. The ablation apparatus system of claim 1, wherein the radially fully extendible spiral wire electrode is extended radially at least twice the diameter of the tubular shaft.

8. The ablation apparatus system of claim 1, wherein the electrode deployment mechanism is adapted to deploy and non-deploy the spiral wire electrode.

9. A method for treating atherosclerosis of a patient having a pre-implanted vascular stent, the method comprising the steps of:
 (a) inserting an ablation apparatus through an artery or a vein to the location of the pre-implanted vascular stent, wherein the ablation apparatus comprises a tubular shaft having a distal section, a distal end, a proximal end, and at least one lumen extending therebetween, wherein the at least one lumen has at least one opening at the distal end of the tubular shaft; a handle attached to the proximal end of the tubular shaft, wherein the handle has a cavity; a hollow tubing having a passageway and a locking valve attached to the handle, wherein the passageway is connected to the at least one lumen of the tubular shaft; an elongate tubular element located inside the at least one lumen of the tubular shaft, wherein the elongate tubular element comprises a distal end and a proximal end, and wherein the distal end comprises a preshaped wire electrode having a plurality of spirals, wherein the diameter of the next spiral is larger than that of the prior spiral; an electrode deployment mechanism mounted on the handle, wherein the electrode deployment mechanism is attached to the proximal end of the elongate tubular element;
 (b) deploying the elongate tubular element to radially fully extend the spiral wire electrode, adapted to contact the pre-implanted stent; and
 (c) applying RF energy to the spiral wire electrode to effect treatment of the atherosclerosis.

10. The method for treating atherosclerosis of a patient having a pre-implanted vascular stent as in claim 9, the method further comprising the ablation apparatus system comprising at least one temperature sensor, wherein the temperature sensor is disposed at close proximity of the spiral wire electrode of the elongate tubular element.

11. The method for treating atherosclerosis of a patient having a pre-implanted vascular stent as in claim 10, the method further comprising the ablation apparatus system comprising a temperature control means, wherein the temperature measured from the temperature sensor is relayed to the temperature control means and adapted to effect the RF energy supply to the spiral wire electrode.

12. The method for treating atherosclerosis of a patient having a pre-implanted vascular stent as in claim 9, the method further comprising the ablation apparatus system having the RF energy delivery within the range of 50 to 2,000 kHz.

13. The method for treating atherosclerosis of a patient having a pre-implanted vascular stent as in claim 9, wherein the material for the spiral wire electrode is selected from the group consisting of platinum, iridium, gold, silver, stainless steel, Nitinol, or an alloy of their mixtures.

14. The method for treating atherosclerosis of a patient having a pre-implanted vascular stent as in claim 9, wherein the radially fully extendible spiral wire electrode is extended radially at least twice the diameter of the tubular shaft.

15. A method for treating tissues of a patient having a pre-implanted medical stent, the method comprising the steps of:
 (a) inserting an ablation apparatus through a natural opening to the location of the pre-implanted medical stent, wherein the ablation apparatus comprises a tubular shaft having a distal section, a distal end, a proximal end, and at least one lumen extending therebetween, wherein the at least one lumen has at least one opening at the distal end of the tubular shaft; a handle attached to the proximal end of the tubular shaft, wherein the handle has a cavity; a hollow tubing having a passageway and a locking valve attached to the handle, wherein the passageway is connected to the at least one lumen of the tubular shaft; an elongate tubular element located inside the at least one lumen of the tubular shaft, wherein the elongate tubular element comprises a distal end and a proximal end, and wherein the distal end comprises a preshaped wire electrode having a plurality of spirals, wherein the diameter of the next spiral is larger than that of the prior spiral; an electrode deployment mechanism mounted on the handle, wherein the electrode deployment mechanism is attached to the proximal end of the elongate tubular element;

(b) deploying the elongate tubular element to radially fully extend the spiral wire electrode, adapted to contact the pre-implanted medical stent; and (c) applying RF energy to the spiral wire electrode to effect treatment of the tissue.

16. The method for treating tissues of a patient having a pre-implanted medical stent as in claim 15, the method further comprising the ablation apparatus system comprising at least one temperature sensor, wherein the temperature sensor is disposed at close proximity of the spiral wire electrode of the elongate tubular element.

17. The method for treating tissues of a patient having a pre-implanted medical stent as in claim 16, the method further comprising the ablation apparatus system comprising a temperature control means, wherein the temperature measured from the temperature sensor is relayed to the temperature control means and adapted to effect the RF energy supply to the spiral wire electrode.

18. The method for treating tissues of a patient having a pre-implanted medical stent as in claim 15, the method further comprising the ablation apparatus system having the RF energy delivery within the range of 50 to 2,000 kHz.

19. The method for treating tissues of a patient having a pre-implanted medical stent as in claim 15, wherein the material for the spiral wire electrode is selected from the group consisting of platinum, iridium, gold, silver, stainless steel, Nitinol, or an alloy of their mixtures.

20. The method for treating tissues of a patient having a pre-implanted medical stent as in claim 15, wherein the radially fully extendible spiral wire electrode is extended radially at least twice the diameter of the tubular shaft.

* * * * *